United States Patent
Hills et al.

(10) Patent No.: US 8,152,978 B2
(45) Date of Patent: Apr. 10, 2012

(54) APPARATUS AND METHOD FOR MEASURING HYDROGEN CONCENTRATION IN MOLTEN METALS

(75) Inventors: Matthew Paul Hills, Cambridgeshire (GB); Mark Anthony Steele Henson, Staffordshire (GB)

(73) Assignee: Environmental Monitoring and Control Limited (GB)

( * ) Notice: Subject to any disclaimer, the term of this patent is extended or adjusted under 35 U.S.C. 154(b) by 647 days.

(21) Appl. No.: 11/664,404

(22) PCT Filed: Oct. 3, 2005

(86) PCT No.: PCT/GB2005/003812
§ 371 (c)(1),
(2), (4) Date: Feb. 4, 2009

(87) PCT Pub. No.: WO2006/037992
PCT Pub. Date: Apr. 13, 2006

(65) Prior Publication Data
US 2009/0127133 A1    May 21, 2009

(30) Foreign Application Priority Data
Oct. 1, 2004  (GB) .................................. 0421868.1

(51) Int. Cl.
*G01N 27/30* (2006.01)
*G01N 27/333* (2006.01)
(52) U.S. Cl. ......... 204/422; 204/431; 204/433; 204/435
(58) Field of Classification Search .................. 204/422, 204/431, 433, 435
See application file for complete search history.

(56) References Cited

U.S. PATENT DOCUMENTS
4,007,106 A   2/1977  Hone et al.
(Continued)

FOREIGN PATENT DOCUMENTS
DE   10203121 A1   8/2003
(Continued)

OTHER PUBLICATIONS

Lapham, D.P., Schwandt, C., Hills, M.P., Kumar, R.V., and Fray, D.J., "The Detection of Hydrogen in Molten Aluminium", *Ionics*, 2002, pp. 391-401, vol. 8.

(Continued)

*Primary Examiner* — Bruce Bell
(74) *Attorney, Agent, or Firm* — Saliwanchik, Lloyd & Eisenschenk

(57) ABSTRACT

The present invention concerns a probe for measuring hydrogen concentration in molten metals comprising a probe body and a hydrogen sensor. The sensor structure is based on a sensor body having a wall within which a sealed cavity is defined. The cavity contains a solid reference material for generating a reference partial pressure of hydrogen within the cavity. At least a portion of the wall of the cavity is formed from a solid electrolyte material carrying a measurement electrode on a surface of the solid electrolyte outside the cavity and a reference electrode on a surface of the solid electrolyte within the cavity, exposed to the reference partial pressure of hydrogen. An electrical conductor extends from the reference electrode through the wall of the cavity to an external surface of the sensor body. The probe body comprises a chamber for receiving the sensor and a reference-signal connection for connecting to the electrical conductor when the sensor is received in the chamber.

22 Claims, 13 Drawing Sheets

U.S. PATENT DOCUMENTS

| | | | |
|---|---|---|---|
| 4,882,032 A | | 11/1989 | Tiwari et al. |
| 5,439,579 A | * | 8/1995 | Koide et al. .................. 204/422 |
| 5,495,746 A | | 3/1996 | Sigworth et al. |
| 6,083,368 A | | 7/2000 | Abe et al. |
| 2004/0084328 A1 | | 5/2004 | Jones et al. |
| 2004/0173473 A1 | | 9/2004 | Habets |
| 2005/0029100 A1 | * | 2/2005 | Park et al. .................. 204/428 |
| 2005/0252789 A1 | * | 11/2005 | Fray et al. .................. 205/775 |

FOREIGN PATENT DOCUMENTS

| | | |
|---|---|---|
| EP | 0544281 A1 | 6/1993 |
| GB | 1594223 | 7/1981 |
| JP | 60-156778 | 10/1985 |
| JP | 2-1538 | 1/1990 |
| JP | 2-73147 | 3/1990 |
| JP | 7-49330 | 2/1995 |
| WO | WO-2004/025289 A1 | 3/2004 |

OTHER PUBLICATIONS

Schwandt, C., Fray, D.J., Hills, M.P., Henson, M.A., Henson, R.M., and Powell, C., "A Novel Electrochemical Analyser for Hydrogen Determination in Aluminium Melts", 2001, 8 pages.

Schwandt, C., Fray, D.J., Hills, M.P., Henson, M.A., Henson, R.M., and Powell, C., "A Novel Electrochemical Hydrogen Analyser for Use in Molten Aluminium and its Alloys", *American Foundry Society*, 2001, 8 pages.

Schwandt, C., Hills, M.P., Henson, M.A., Fray, D.J., Henson, R.M., and Moores, A., "Determination of Hydrogen in Molten Aluminium and its Alloys Using and Electrochemical Sensor", *EPD Congress The Minerals, Metals & Materials Society*, 2003, pp. 427-438.

Yajima, T. et al. "Application of hydrogen sensor using proteon conductive ceramics as a solid electrolyte to aluminum casting industries" *Solid State Ionics*, 1995, 79:333-337.

English language translation of a Notice of Reasons for Rejection issued in Japanese Patent Application No. 2007-534092.

* cited by examiner

APPARATUS AND METHOD FOR MEASURING HYDROGEN CONCENTRATION IN MOLTEN METALS

This application is the U.S. national stage application of International patent application No. PCT/GB2005/003812, filed Oct. 3, 2005.

The invention relates to an apparatus and a method for measuring hydrogen concentration, and in particular for measuring dissolved hydrogen concentration in molten metals.

BACKGROUND OF THE INVENTION

It is important to monitor the concentration of hydrogen dissolved in molten metals, and in particular in molten aluminium and its alloys. The solubility of hydrogen in molten aluminium is much higher than its solubility in solid aluminium, and therefore when aluminium is cast there is a tendency for dissolved aluminium in the melt to form bubbles or other flaws in the solid aluminium product. The hydrogen concentration in molten aluminium can rise through reaction of the aluminium with moisture in the environment, and so it is critical to be able to monitor hydrogen concentration during aluminium casting.

Many methods have been developed for monitoring hydrogen concentration in molten aluminium and its alloys, and in other metals, but all of these suffer disadvantages such as lack of accuracy, a requirement for cumbersome apparatus, and disadvantageously long measurement times. A technology which offers solutions to these problems is the possibility of using a proton-conducting solid-electrolyte sensor with an internal solid-state hydrogen reference. This technology has been described in published prior art, including 'The Detection of Hydrogen in Molten Aluminium' by D P Lapham et al, Ionics 8 (2002), pages 391 to 401, 'Determination of Hydrogen in Molten Aluminium and its Alloys using an Electrochemical Sensor' by C Schwandt et al, EPD Congress 2003, TMS (The Minerals, Metals and Materials Society), 2003, pages 427 to 438, and in International patent application No. PCT/GB2003/003967 of Cambridge University Technical Services Limited. All of these documents are incorporated herein by reference in their entirety. An advantageous method for taking measurements from such a probe, termed the 'reverse current technique' has been described in European patent application No. EP 98932375.3 of D J Fray and R V Kumar, which is also incorporated herein by reference in its entirety.

However, this technology has not, to date, been developed to produce a hydrogen probe which meets the practical requirements of shop-floor use in a foundry. The present invention aims to address this problem.

SUMMARY OF THE INVENTION

The invention provides in its various aspects a probe, a hydrogen sensor and a method as defined in the appended independent claims. Preferred or advantageous features of the invention are defined in dependent sub-claims.

In a first aspect the invention may thus advantageously provide a probe comprising a probe body and a hydrogen sensor. The sensor is preferably a proton-conducting solid-electrolyte sensor with an internal solid-state hydrogen reference contained within a sealed cavity in a sensor body. The solid electrolyte forms at least a portion of a wall of the sensor body and has a reference electrode on at least a portion of its surface within the cavity. The solid reference material generates a reference partial pressure of hydrogen within the cavity, to which the reference electrode is exposed. The reference electrode is connected to an electrical conductor which extends through the wall to an external surface of the sensor body.

The probe body preferably comprises a chamber for receiving the sensor and a reference-signal connection, or connector, for connecting to the electrical conductor when the sensor is received in the chamber. The reference-signal connection may then be electrically connectable to an analyser for generating hydrogen concentration measurements. In a preferred embodiment, the sensor may be insertable into the chamber in the probe body and the reference electrode automatically connected to the reference-signal connection as the sensor is inserted.

It is also necessary for the analyser to be electrically connected to a measurement electrode formed on at least a portion of a surface of the solid electrolyte outside the cavity. This may be achieved, for example, either by a second electrical conductor extending from the measurement electrode, or by means of an electrical path through the molten metal in which the probe is immersed during hydrogen sensing.

Advantageously, the probe body is carried at the end of a probe support, so that at least an end of the probe body can be immersed in molten metal for sensing hydrogen concentration. In a preferred embodiment, an opening is defined at the end of the probe body which is to be immersed in the molten metal. The sensor is advantageously insertable through the opening into the chamber in the probe body and the opening is then sealable by means of a hydrogen-permeable seal. Thus, when the probe body is immersed in molten metal, the metal does not pass through the seal but hydrogen from the melt diffuses through the seal and generates a partial pressure of hydrogen within the chamber. The measurement electrode on the solid electrolyte is exposed to the hydrogen and a potential difference across the solid electrolyte is generated, which is related to the ratio between the partial pressures of hydrogen at the measuring electrode and at the reference electrode in known manner, according to the Nernst equation. The analyser described above can then measure the potential difference, or use a technique such as the 'reverse current technique' to determine the hydrogen partial pressure in the chamber, given that the reference hydrogen partial pressure is known.

If the measurement electrode is connected to the analyser by means of an electrical conductor extending from the measurement electrode, the hydrogen-permeable seal may comprise a conductive or a non-conductive material. Alternatively, the seal may be electrically conductive and form part of a conduction path from the measurement electrode to the molten metal. A separate electrical connection is then made between the molten metal and the analyser. In one embodiment, a conductive hydrogen-permeable seal comprises graphite, for example in the form of graphite wool or a porous graphite layer. If a graphite seal is used, particularly in a probe for sensing hydrogen concentration in aluminium or an aluminium alloy, the outer surface of the graphite is advantageously coated with titanium diboride to improve wetting with the molten aluminium.

In order to reduce the response time of the probe, it may be advantageous to reduce the volume of hydrogen which needs to diffuse into the chamber in order to achieve a hydrogen partial pressure which is in equilibrium with the hydrogen concentration in the melt. To achieve this, in a preferred embodiment the volume of the chamber (termed the chamber 'dead volume') is decreased by placing an insert between the hydrogen-permeable seal and the sensor.

Advantageously, the hydrogen-permeable seal may be used mechanically to retain the sensor in the chamber, for example by making the seal an interference fit in the opening at the end of the chamber or by making the seal part of a screw cap covering the opening.

Advantageously, the seal is removable to allow removal and replacement of the sensor, for example in the event of sensor failure.

Advantageously, the chamber in the probe body is hermetically sealed except at the opening. Thus, no seal between the sensor and the chamber body may be required, either to prevent diffusion of hydrogen out of the chamber or environmental access into the chamber. Advantageously, therefore, the arrangement of the reference-signal connection of the probe body is hermetically sealed.

In a preferred embodiment, the sensor body is not fastened to the probe body and is advantageously a loose fit in the chamber. In other words, there is preferably sufficient clearance between the sensor and the chamber to accommodate thermal shocks or relative thermal expansion of the sensor body and the probe body, to avoid the application of excessive stresses to the sensor. Otherwise, such thermal stresses may damage the sensor. This clearance may also permit hydrogen flow between the sensor body and the chamber, which may enable the measurement electrode to be positioned at any point on the surface of the probe body, and not necessarily at the surface of the probe body nearest to the opening in the probe body.

In an alternative embodiment, the probe body may not comprise a chamber for receiving the probe; in this embodiment, the probe body is integral with the sensor. In this embodiment the probe body may advantageously enable some or all of the functions of providing a hydrogen-permeable seal between the melt and the solid electrolyte, protecting the sensor from the melt, and providing a means for coupling the sensor to a probe support. In one such embodiment, the sensor tube may be incorporated within a protective ceramic sleeve which is shaped to receive the hydrogen-permeable seal at one end and to fit onto the probe support, for example by means of a push fit, at the other end. Alternatively, the probe body may provide only an external coating to protect the sensor. In a further alternative the probe-body coupling means, for coupling the sensor to the probe support, may comprise a radially-extending flange at an end of the sensor tube, adapted to engage with a coupling such as a threaded collar to secure it to the probe support. In a further embodiment, the function of the hydrogen-permeable seal may be implemented by inserting the seal into a suitably extended portion of the sensor tube, which extends away from the sensor chamber beyond a planar solid electrolyte seated on a recessed seat within the tube.

In each of these embodiments in which the sensor is integrated with the probe body, the probe body incorporating the sensor may advantageously be releasably couplable to the probe support, as in other embodiments described herein, in order to achieve the advantage of being able to replace the probe body and the sensor after degradation or damage during use.

The dimensions of the components of the probe and the materials from which the various components are made may advantageously be selected to ensure that the probe is robust and reliable when subjected to the thermal shock and cycling involved in repeated immersion in molten metal.

Advantageously, the probe is of small size (particularly of small lateral dimension, or diameter). For example the maximum lateral dimension of the sensor body is advantageously less than 10 mm, preferably less than 6 mm and particularly preferably less than 4 mm. This may not only reduce the effects of thermal shock but also advantageously decrease the time taken for the probe to reach operating temperature when immersed in molten metal and improve the response time of the probe by reducing the volume of the probe body chamber and the dead volume therein for the diffusion of hydrogen.

In a preferred embodiment, the solid electrolyte comprises a perovskite, such as indium-doped calcium zirconate. Other portions of the sensor body are advantageously fabricated from materials of thermal expansion coefficient compatible with the solid electrolyte. For example, the remainder of the sensor body may have the same thermal expansion coefficient as the solid electrolyte or a slightly smaller thermal expansion coefficient so as to keep the solid electrolyte in compression at elevated temperature, to prevent cracking of the electrolyte.

The solid reference material advantageously comprise a metal/metal hydride reference, such as titanium/titanium hydride, zirconium/zirconium hydride or hafnium/hafnium hydride.

The electrodes on the surfaces of the solid electrolyte are preferably porous platinum electrodes.

The probe body is preferably fabricated from a material or materials which are substantially inert when immersed in the molten metal, which provide good thermal shock resistance and which have a suitable thermal expansion coefficient to avoid applying stresses to the sensor body. In preferred embodiments, the probe body may comprise aluminium nitride, SiAlON, silicon nitride, dense graphite, alumina, magnesia, boron carbide or stabilised zirconia. The probe body may advantageously be coated with a wetting agent or with titanium diboride. The latter is particularly effective if the probe body is made of graphite and is for immersion in molten aluminium.

The probe may form part of a probe assembly, in which the probe body is mounted at one end of a probe support. The other end of the probe support may be provided with a handle for an operator to hold to immerse the probe in the melt. The probe support may be tubular, in which case electrical connections may be carried along its interior between the probe body and the analyser.

The end of the probe support may be fastened to the probe body in any convenient manner. In one embodiment, the probe support is fastened to the probe body by brazing or by means of silica-free glass. In such an embodiment, the end of the probe support may form part of the wall of the probe body chamber, in which case the joint between the probe support and the probe body is advantageously hermetically sealed. If the probe support is in the form of a tube carrying, for example, a conductor leading from the reference electrode, then the tube should advantageously be sealed, for example using silica-free glass.

In an alternative embodiment the probe body, including (if present) the chamber for receiving the sensor and the sensor itself, may be constructed as a replaceable unit. Similarly, a probe body incorporating a sensor as an integral unit, as described above, may be constructed as a replaceable unit or component. In these embodiments the probe body may advantageously be designed to be removably couplable to an end of the probe support for easy replacement. During use, the probe body and, depending on the design of the probe, a portion of the probe support are repeatedly immersed in molten metal and may therefore degrade. It may therefore be economically advantageous to make the probe body replaceable. In a preferred implementation of this embodiment, a coupling between the probe body and the probe support both mechanically supports the probe body during use and makes any required electrical connections, including (as applicable)

any connections to the reference electrode, the measurement electrode and a thermocouple.

In an example of this embodiment a probe-body chamber, in which a sensor is received, is mounted at one end of a probe-body shaft. The shaft has an external surface which is substantially inert to a molten metal in which the probe is to be used and carries internally along its length any required electrical conductors. For example, a thermocouple and a connection to the reference electrode may extend within the shaft, while the melt is used to provide a connection to the measurement electrode as described above. The end of the probe-body shaft distant from the sensor is provided with a suitable coupling for securing it to an end of the probe support. The coupling may conveniently comprise a threaded graphite coupling; since the graphite is electrically conducting this may make contact with the melt during measurements and so be used to complete a conduction path from the measurement electrode through the melt to an electrical conductor housed within the probe support. The probe support may advantageously be tubular and carry electrical conductors internally, protected from the melt, to a handle end of the support for taking readings from the sensor.

This design may advantageously allow fast and easy replacement of the probe body and the sensor, which may then be serviced or discarded. The replaceable unit contains substantially all of the components of the probe that are subject to deterioration, such as the hot-end seal (sealing the probe chamber) and the sensor itself. Advantageously, the probe is designed so that replacement of the probe body does not require an operator to connect any electrical connections manually; these are advantageously automatically completed as the probe body is coupled to the probe support.

A probe embodying the invention may be used for measuring the concentration of hydrogen in molten metals such as aluminium, magnesium or copper or alloys of these metals. Depending on the materials used for fabricating the probe, and their thermal performance, it may be necessary to mount the sensor at a distance from the probe body opening. For example, the probe as described above may advantageously be used with molten aluminium, magnesium or their alloys but copper and its alloys generally melt at higher temperatures. Thus, for aluminium, magnesium and their alloys the sensor may be mounted close to the opening from the probe chamber in order to minimise the chamber volume and reduce the probe's response time. For use with copper and copper alloys, in order to expose the sensor to lower temperatures it may be necessary to mount the sensor further from the opening at the end of the probe body chamber, and thus further from the molten metal.

In a further aspect, the invention provides a hydrogen sensor constructed as follows. The sensor body comprises a tube, with a solid electrolyte closing one end of the tube and a sensor cap closing the other end of the tube, so as to define a sealed cavity within the sensor body. A solid reference material within the cavity, which is preferably a metal/metal hydride reference, generates a reference partial pressure of hydrogen within the cavity. A measurement electrode is provided on a surface of the solid electrolyte outside the cavity and a reference electrode is provided on a surface of the solid electrolyte within the cavity, exposed to the reference partial pressure of hydrogen. An electrical conductor extends from the reference electrode to an external surface of the sensor body, preferably through an opening in the sensor cap, which is sealed by brazing or by a silica-free glass. In this embodiment, the solid electrolyte is preferably substantially planar. Advantageously, the tube may be of circular section and the solid electrolyte substantially disc-shaped.

Preferably the maximum lateral dimension of the solid electrolyte is less than 10 mm, preferably less than 6 mm and particularly preferably less than 4 mm.

Advantageously, the cavity contains a buffer material between the reference material and the sensor cap. This may not only advantageously reduce the volume of the cavity containing the reference partial pressure of hydrogen but may also protect the reference material from exposure to the brazing or sealing process required to secure the sensor cap to the tube.

This and the other aspects of this invention described above may, in preferred embodiments, provide a probe for measuring hydrogen concentration in a molten metal which addresses the problems of prior art probes. In particular, embodiments of the invention may provide probes which are robust, of conveniently small size and which provide accurate measurements with rapid response times. In addition, economical performance over extended times and during repeated immersion in molten metal may be achieved in a preferred embodiment in which the sensor is removable from the probe body and replaceable with a new sensor, or in which the probe body incorporating the sensor is removable from the probe support and replaceable.

DESCRIPTION OF SPECIFIC EMBODIMENTS AND BEST MODE OF THE INVENTION

Specific embodiments of the invention will now be described by way of example, with reference to the drawings, in which.

DETAILED DESCRIPTION OF THE INVENTION

Figure 1:
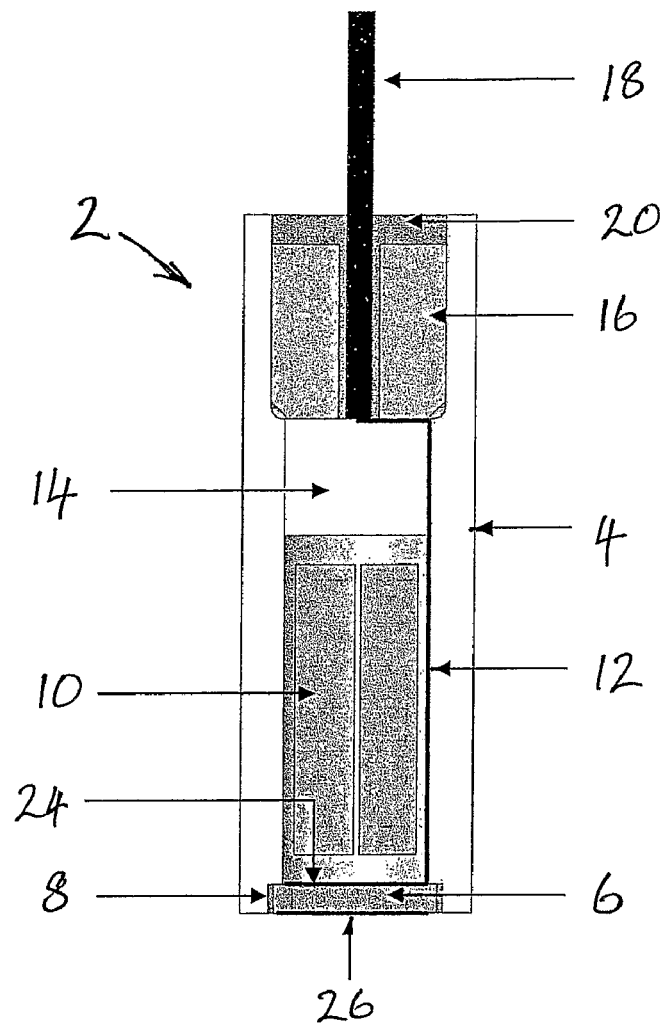
FIG. 1 is a longitudinal section of a hydrogen sensor according to a first embodiment of the invention.

FIG. 1 is a longitudinal section of a hydrogen sensor 2. The sensor has a sensor body comprising a tube 4, closed at one end by a planar solid-electrolyte disc 6. The disc has a porous platinum electrode 24, 26 formed on each surface and is sealed into a recess in the end of the tube using a silica-free glass 8. A metal-metal hydride reference material 10 is inserted into the tube behind the reference electrode and an electrical conductor 12 extends from the reference electrode along an internal wall of the tube. A volume within the tube above the reference material is filled with an inert buffer material 14 such as $Y_2O_3$ powder. A sensor cap 16 is then inserted into an upper end of the tube. An electrode wire 18 extending through a hole in the sensor cap makes contact with the electrical conductor 12. The electrode wire is sealed in the hole and the sensor cap is sealed to the tube using a glass seal 20, preferably of a silica-free glass. The solid electrolyte disc, the tube and the sensor cap form the walls of a sensor body enclosing a sealed cavity. The cavity contains the solid reference material, which generates a reference hydrogen partial pressure within the cavity. The electrode wire extends outwardly from the sensor body, coaxial with the tube.

The solid electrolyte is preferably of indium-doped calcium zirconate. The tube and the sensor cap are preferably manufactured from undoped calcium zirconate, in which case the thermal expansion of the tube is matched to that of the electrolyte disc and the sensor cap, allowing the sensor to be thermally cycled without the build up of excessive thermal stresses. Alternatively, the tube and sensor cap can be manufactured from magnesia-magnesium aluminate (MMA), which has a thermal expansion coefficient slightly higher than the indium-doped calcium zirconate electrolyte. In this case, the electrolyte is permanently in a state of compressive stress under measurement conditions (immersed in molten metal), increasing the thermal shock and thermal cycling resistance of the electrolyte.

The diameter of the electrolyte disc in the embodiment is 3 mm and the outer diameter of the tube is 4 mm.

Figure 2:
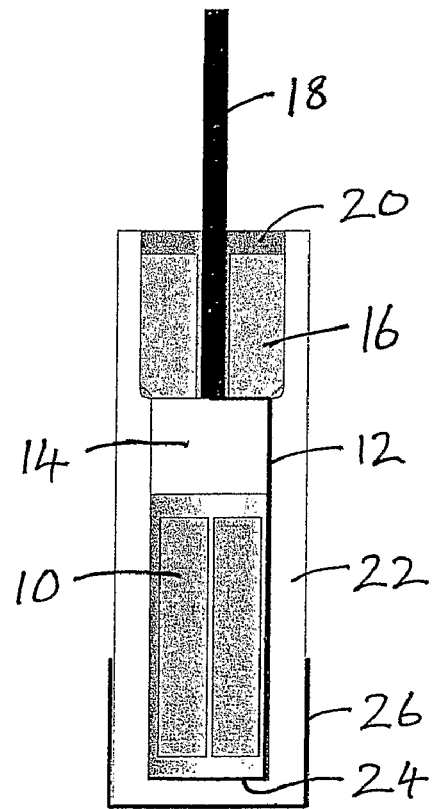
FIG. 2 is a longitudinal section of a hydrogen sensor according to a second embodiment of the invention.

FIG. 2 illustrates an alternative sensor which differs from the sensor of FIG. 1 in that the tube and the solid electrolyte disc are fabricated as a single component, termed a thimble 22. Thus, in this case, the wall of the sensor body consists of a closed-ended indium-doped calcium zirconate tube, which is closed at its open end by a sensor cap and an electrode wire in the same way as the sensor of FIG. 1. Components common to FIGS. 1 and 2 are given the same reference numerals in both Figures.

Figure 3:
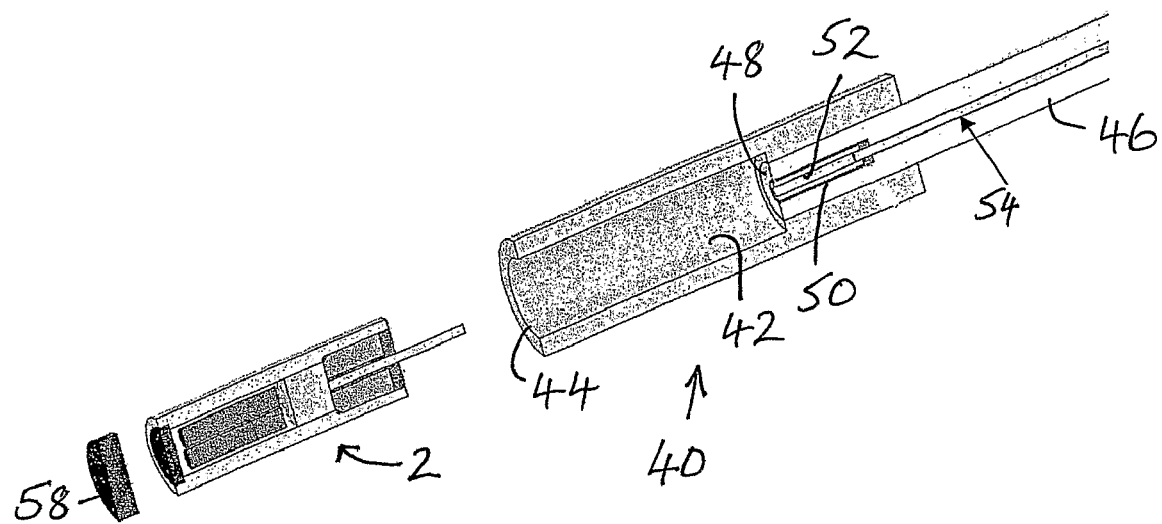
FIG. 3 is an exploded sectional view of a probe incorporating the sensor of FIG. 1.
Figure 4:
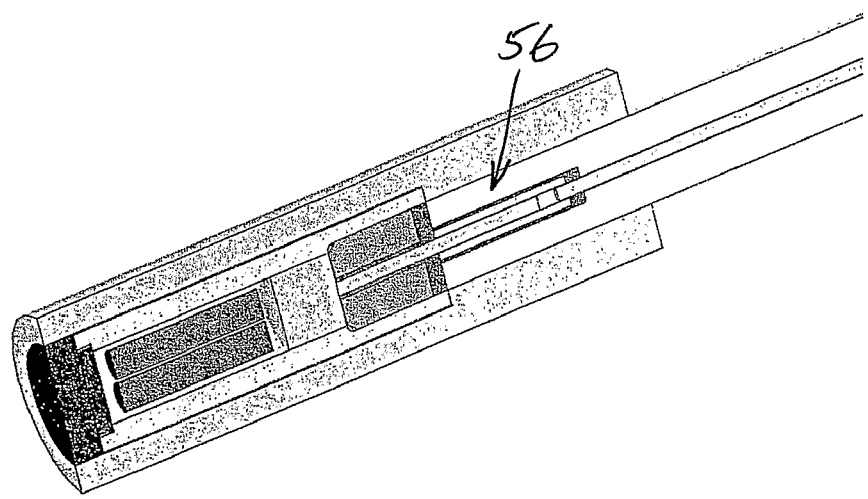
FIG. 4 is an assembled sectional view of the probe of FIG. 3.

FIGS. 3 and 4 illustrate the assembly of a probe comprising a probe body 40 and a sensor 2, as shown in FIG. 1. FIG. 3 is an exploded view of the probe and FIG. 4 is an assembled view of the probe.

The probe body encloses a probe body chamber 42 which terminates at an opening 44. The probe body is of generally cylindrical shape and at the end of the chamber opposite the opening, a central bore in the probe body receives an end of a probe support 46. An end 48 of the probe support forms a portion of an end surface of the chamber and is brazed or sealed to the probe body. A blind bore 50 lined with a metallic tube 52 extends coaxially from the chamber within the probe support. The blind bore terminates at an electronic conductor 54 which runs along central bore within the probe support. The end of the electronic conductor is sealed at the end of the blind bore using brazing or a glass seal to ensure that the end of the chamber is hermetically sealed.

The chamber 42 is shaped so as to receive the sensor 2 and, when the sensor is fully inserted in the chamber, the electrode wire 18 enters and makes electrical contact with the metal tube 52, which thus forms a reference electrode connection 56, as shown in FIG. 4. After the sensor has been inserted into the chamber, a hydrogen-permeable seal or barrier 58 is inserted, as an interference fit, into the opening 44, closing the chamber and mechanically retaining the sensor within the chamber.

Advantageously, there is sufficient clearance between the sensor and the probe body to allow free expansion and contraction of the sensor during the thermal cycling caused by immersion of the probe into molten metal, without the sensor body being constrained by the probe body as the probe is heated and cooled.

With the sensor is in place within the chamber and the hydrogen-permeable seal in place, the hermetic sealing of the chamber at its sides and at its end opposite the hydrogen-permeable seal prevents any leakage of hydrogen out of the measuring chamber when measurements are made and protects the sensor from environmental contamination.

The hydrogen-permeable seal prevents direct contact between the molten aluminium and the solid electrolyte or other components of the sensor. It is important that direct contact between molten aluminium and the electrolyte should be avoided as this causes the electrolyte to leave the hydrogen-ion-conduction domain and to enter the oxygen-ion-conduction domain. In that case, the potential of the measurement electrode would be determined by the oxygen activity at that electrode rather than the activity of hydrogen, leading to erroneous readings. The hydrogen-permeable seal is, however, electrically conductive and serves to make an electrical connection between the measuring electrode and the molten metal. An analyser can therefore make electrical contact with the measurement electrode through the melt, and with the reference electrode through the electronic conductor within the probe support. Graphite felt, graphite wool or a grade of graphite with open porosity are suitable materials for the hydrogen-permeable barrier in this embodiment.

The probe body is preferably made of a material of high density, to avoid any gaseous diffusion through the chamber walls, of high thermal shock resistance, in order to allow rapid immersion into the melt without breakage, of low thermal expansion coefficient, and which is chemically stable in contact with the molten metal during measurement. Machineable-grade aluminium nitride is a suitable material as it allows the body to be manufactured cheaply by machining, preferably with no grinding being required. Other suitable materials for the probe body are SiAlON, silicon nitride, dense graphite, alumina, magnesia, or stabilised zirconia.

The probe body and the hydrogen-permeable barrier are preferably painted with a titanium diboride ink. By coating the probe body in this manner, the response time upon immersion in molten aluminium or aluminium alloys and the response of the probe to changes in dissolved hydrogen level may be considerably improved. The $TiB_2$ coating enhances wetting in molten aluminium and is electrically conductive, and so improves electrical contact between the melt and the hydrogen-permeable barrier and the remainder of the probe body. This may be advantageous for example during degassing of the molten metal, when gas bubbles passing beneath the probe tend to cause loss of electrical contact with the melt, leading to erratic and unreliable readings. Coating the probe body with $TiB_2$ ink helps prevent loss of electrical contact as the coating provides an electrical contact around the entire surface of the probe body. Any suitable electronically conductive coating which is stable in the metal melt may also be used for this.

The probe support should be made from an electrically-insulating material to prevent a short circuit between the reference and measurement electrodes when the probe is immersed in the melt. Alumina is a suitable material for the probe support as long as its diameter is sufficiently small (3 mm or less) to avoid damage due to thermal cycling. Other suitable materials are SiAlON or silicon nitride. Importantly, any thermal expansion mismatch between the probe support and the probe body should be taken into account to ensure that the two are held tightly together when the probe is heated to its operating temperature.

Figure 5:
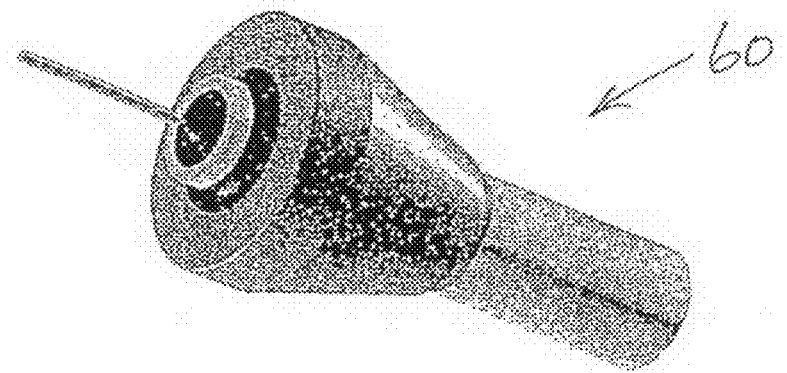
FIG. 5 is a three-quarter view of a sensor according to a third embodiment of the invention.
Figure 6:
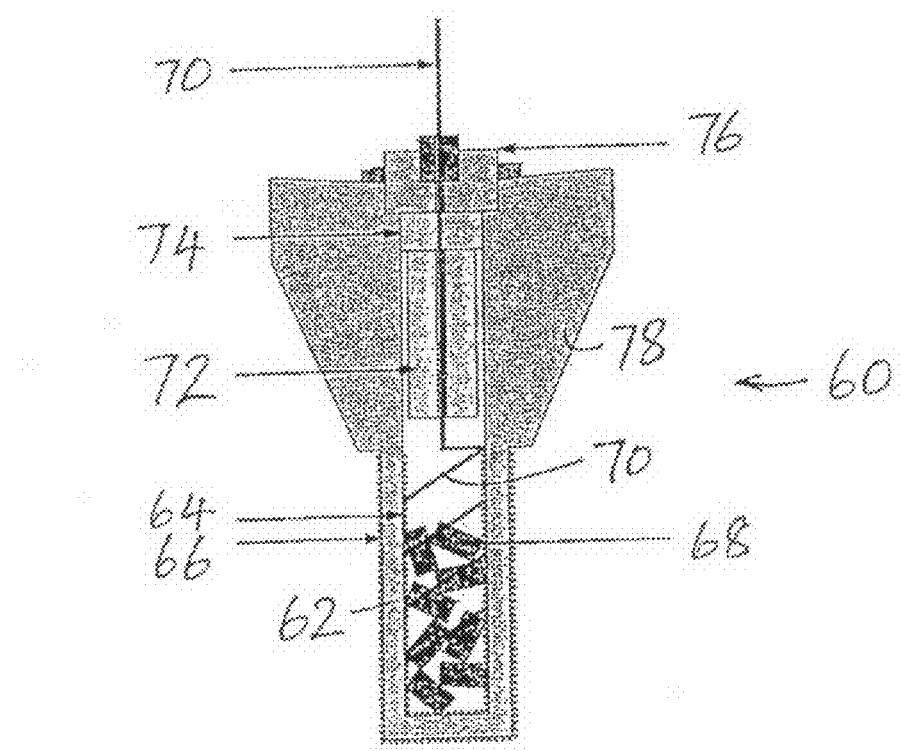
FIG. 6 is a longitudinal section of the sensor of FIG. 5.

FIG. 5 illustrates a third sensor 60, shown in longitudinal section in FIG. 6. The structure of this sensor is similar to that of FIG. 2 in that it is formed from a tube of solid electrolyte material 62 closed at one end and having a reference electrode 64 and a measurement electrode 66 formed on its inner and outer surfaces respectively. A metal-metal hydride reference material 68 is inserted into the tube and an electrical conductor 70 extends from the reference electrode within the tube. The conductor is helically shaped where it contacts the reference electrode in order to contact a large area of the reference electrode. A spacer 72 is inserted into the tube above the reference material, and the electrical conductor extends through a central bore within the spacer. An upper end of the tube is packed with an inert buffer material 74 and closed by a sensor cap 76. The electrical conductor extends through a central bore in the sensor cap. The sensor cap is sealed to the tube and the conductor using glass seals or brazing. The external diameter of the tube surrounding the spacer progressively increases to form a frusto-conical external surface 78, which provides accurate location of the sensor within a correspondingly-shaped probe body as described below.

The materials for fabricating the sensor of FIGS. 5 and 6 are as for the sensor of FIG. 2. The spacer 72 is made from an inert material such as aluminium oxide and takes up dead volume in the sensor cavity in order to reduce the response time of the sensor.

Figure 7:
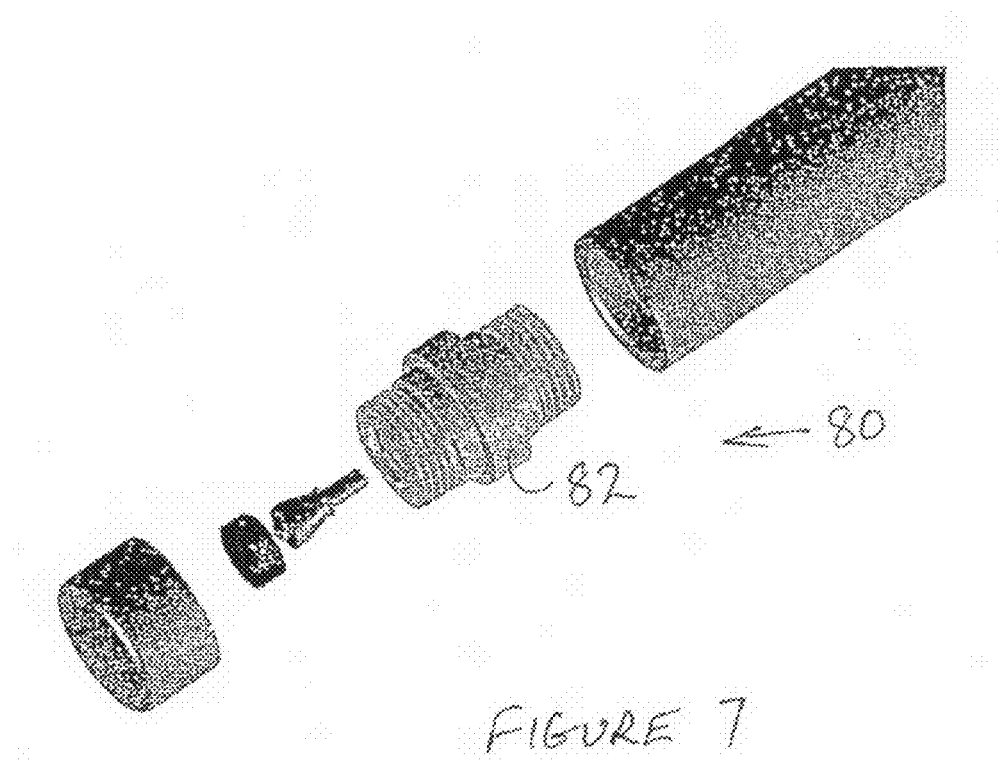
FIG. 7 is an exploded view of a probe incorporating the sensor of FIG. 5.
Figure 8:
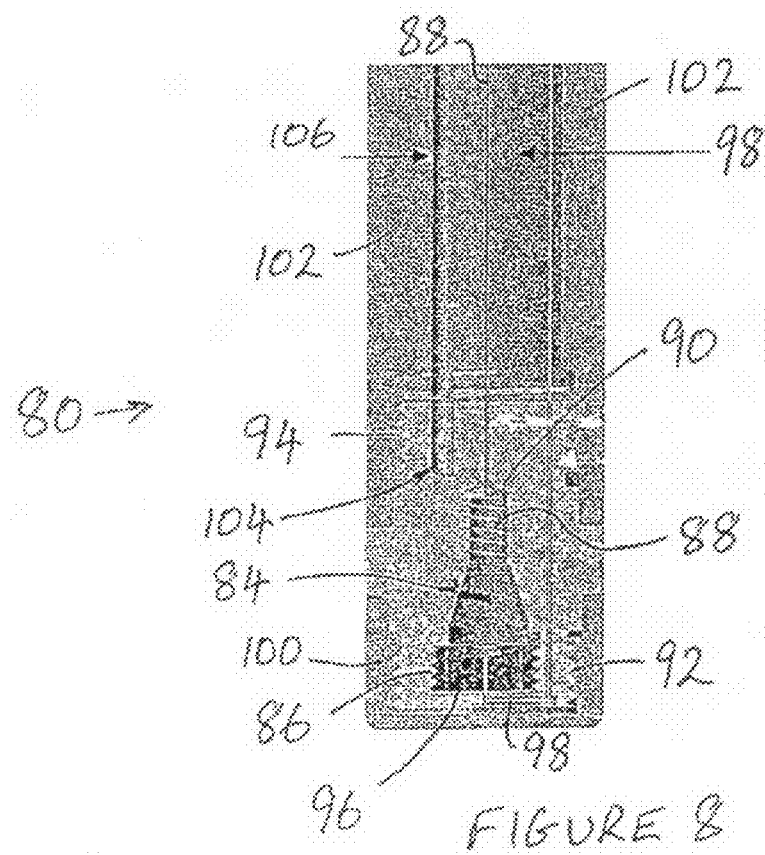
FIG. 8 is a longitudinal section of the probe of FIG. 7, in its assembled form.

FIGS. 7 and 8 are exploded and assembled views of a modular probe 80 for receiving the sensor of FIGS. 5 and 6. A probe body 82 of generally cylindrical shape has an internal wall defining a probe chamber 84 aligned with its axis of symmetry. The probe chamber ends at an internally threaded opening 86 at one end of the probe body. An electrical conductor 88 is wound helically within the blind end 90 of the probe chamber and extends through and is sealed within a central bore in the probe body extending from the blind end of the chamber.

The probe body is externally threaded at both ends 92, 94.

The probe chamber is shaped to receive the sensor of FIGS. 5 and 6, with the end of the sensor carrying the measurement electrode being inserted into the blind end of the chamber so that the measurement electrode makes as contact with the electrical conductor 88. An externally-threaded insert 96 is then threaded into the internal thread 86 at the end of the probe chamber to retain the sensor in position. The electronic conductor extending from the reference electrode passes through a central bore in the threaded insert and makes contact with a further electrical conductor 98 which passes through a sealed bore within the probe body and emerges parallel to the electronic conductor 88 connected to the measurement electrode.

An internally-threaded cap 100 is threaded on to the external thread 92 of the probe body to provide a hydrogen-permeable seal at the opening of the probe chamber.

The thread 94 at the other end of the probe body is threaded into an end of a tubular probe support 102, the measurement and reference electronic conductors passing along the inside of the tube. The end of the probe body within the probe support further comprises a recess 104 for receiving an end of a thermocouple 106 for measuring the temperature of the probe body adjacent to the sensor. The measurement and reference electronic conductors and the leads from the thermocouple pass along the tubular probe support for connection to an analyser for measuring hydrogen concentration and temperature.

In the same way as for the probe of FIGS. 3 and 4, in this embodiment there is sufficient clearance between the sensor and the walls of the probe chamber to allow the sensor to expand and contract freely without being constrained by the probe body when the probe is heated and cooled. In addition, sufficient clearance is provided to allow hydrogen flow around the sensor to the region of the measurement electrode.

The measurement and reference electronic conductors are both sealed where they run through the probe body, using silica-free glass or by brazing, to ensure hermetic sealing of the probe chamber (other than at the hydrogen-permeable seal).

The hydrogen-permeable seal is provided by the porous cap 100, which allows the exchange of hydrogen between the melt and the probe chamber whilst preventing aluminium ingress into the chamber. If the cap is made from a porous grade of graphite, it is preferably coated with titanium diboride to ensure good wetting, and hence good hydrogen exchange, with molten aluminium. However, the cap may be manufactured from other materials, such as porous ceramic materials (e.g. porous alumina, porous silicon carbide, porous silicon nitride) or metallic foam. If these materials are used, it may not be necessary to use a titanium diboride coating on the cap in order to obtain an adequate probe response. Nevertheless, employing a titanium diboride coating should improve the probe response. It may be noted that because the both measurement and reference electrodes are connected by electronic conductors to the analyser, there is no need for electrical connection to the melt, so the hydrogen-permeable seal may be made using an electrically-insulating material.

If the probe cap 100 is of an electronic conductor, such as graphite or metallic foam, an earth lead may be provided to link the cap, through the interior of the probe support tube, to earth in order to reduce electrical noise in the sensor signal.

Selection of the probe body material is as for the probe of FIGS. 3 and 4 except that it must be of an electrically-insulating material in order to prevent short circuiting of the measurement and reference electronic conductors and, if present, the earth wire. Suitable materials are SiAlON, silicon nitride, and boron carbide.

The probe support should be made from a material providing good thermal shock resistance, chemical stability in contact with the molten metal, and chemical stability in air over the measurement temperature range, which for molten aluminium is typically 650 to 800C. Suitable materials include SiAlON, silicon nitride, aluminium nitride and boron carbide. Graphite may also be used but may require a protective coating, such as aluminium orthophosphate, or regular replacement due to its decomposition in air at between 650° C. and 800° C.

In each of the described embodiments of the invention, the stability of the electrical signals from the sensor and, if present, from the thermocouple, may be improved by screening the electrical conductors carrying the signals from electrical noise. In a preferred embodiment in which the conductors are directed within a tubular probe support, this may be achieved by connecting the probe support to earth if the probe support material is manufactured from an electrically-conducting material such as graphite. If the probe support is made from an insulating material, its internal wall may be coated with an electrically-conducting oxidation-resistant material such as silver, gold or platinum, which is then electrically connected to earth. Electrically-conducting materials with poor oxidation resistance may also be used, such as copper, if the layer of conducting material is protected from exposure to oxygen by, for example, a glass coating. In an alternative embodiment, screening may be achieved by running the electrical conductor or conductors (suitably insulated) within an additional metal tube of, for example, steel or inconel, placed inside and concentric with the tubular probe support, electrically connected to earth.

Figure 9:
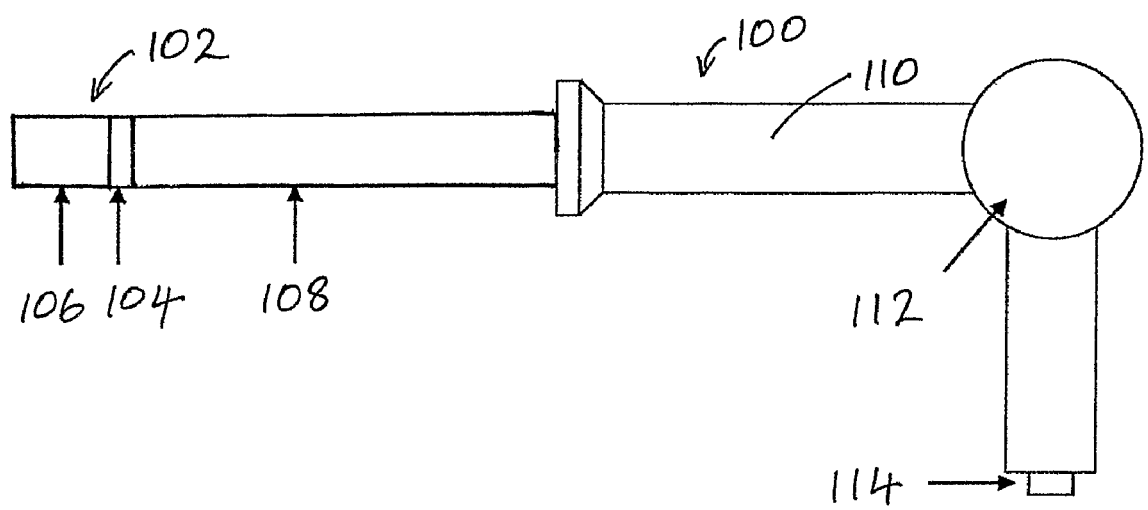
FIG. 9 is schematic view of a probe assembly embodying the invention.

FIG. 9 is a schematic illustration of a probe assembly 100.

As shown in FIG. 9, a probe 102 comprising a probe body 104 terminates at a hydrogen-permeable cap 106, similar to the structure illustrated in FIG. 8. The probe is carried on a tubular probe support 108, within which are housed electrical conductors carrying signals from the sensor mounted within the probe body and from a thermocouple. The end of the probe support distant from the probe is mounted in a bore within a metal handle 110. It is important that the probe support is held firmly in place such that any thermal expansion mismatch between the probe support and the handle does not result in the probe support cracking, or becoming loose, upon heating. In the embodiment this is achieved by forming a circumferential groove on the outer surface of the probe support, into which a copper ring is fitted. As the probe support is is inserted into the bore in the handle, the copper ring enters the bore and three grub screws positioned around the circumference of the handle then screw in, in a radial direction, on to the copper ring. This not only ensures a secure fastening but achieves an electrical connection between the copper ring and the handle, which can be employed to earth the probe support. If the probe support is of a conducting material, then the earth connection is achieved automatically. If the probe support is of an insulating material and is internally screened, a connection between the screen and the copper ring should be made. For example, if the probe support is internally coated with a metal coating, the coating can be extended to the outside of the probe support such that it contacts the copper ring.

The handle 110 terminates at a hub 112 from which an electrical socket 114 extends. The hub houses a ceramic connector block to which the electrical conductors from the sensor and the thermocouple (if present) are connected. Corresponding connections extend from the connector block to the electrical connector 114, which can be connected to an electronic analyser, preferably by means of a screened cable. The analyser can then generate hydrogen concentration and temperature measurements from the probe.

FIGS. 10 to 15 illustrate various aspects of a probe according to a further embodiment of the invention.

Figure 10:
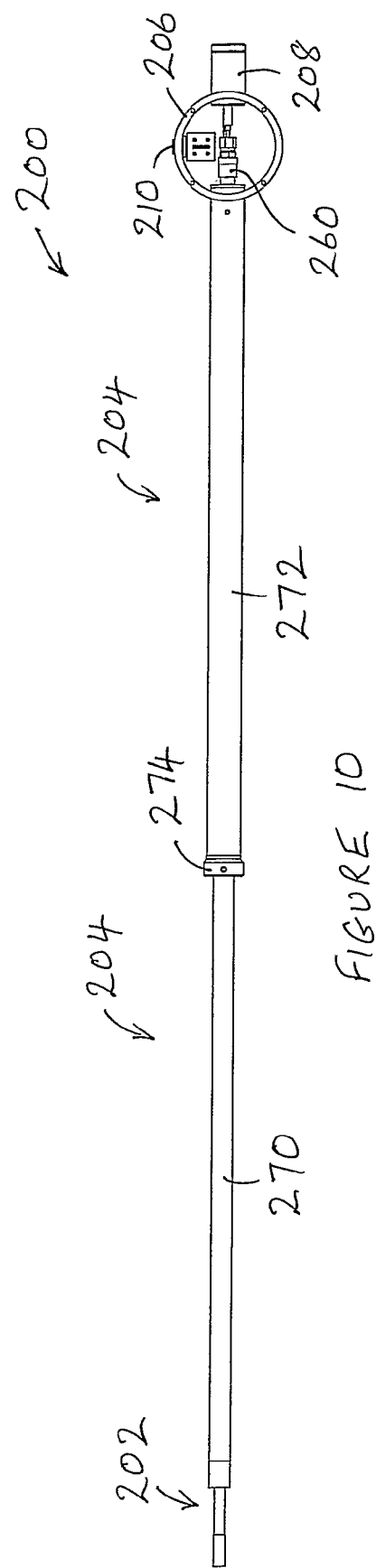
FIG. 10 is a side view of a probe according to a further embodiment of the invention.

FIG. 10 is a side view of the assembled probe 200 incorporating a probe body 202 coupled to a probe support 204. The end of the support distant from the probe body terminates at a hub 206 and a handle 208. The hub comprises a connector or connection block 210 for electrical connection of the probe to an electronic analyser.

Figure 11:
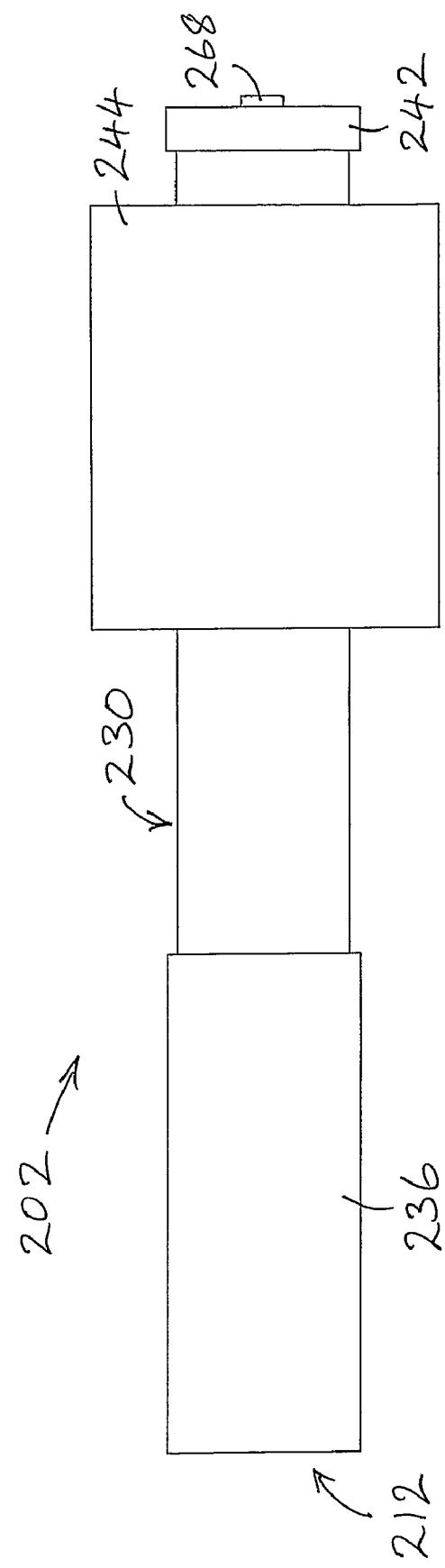
FIG. 11 is a side view of the probe body of the probe of FIG. 10.
Figure 12:
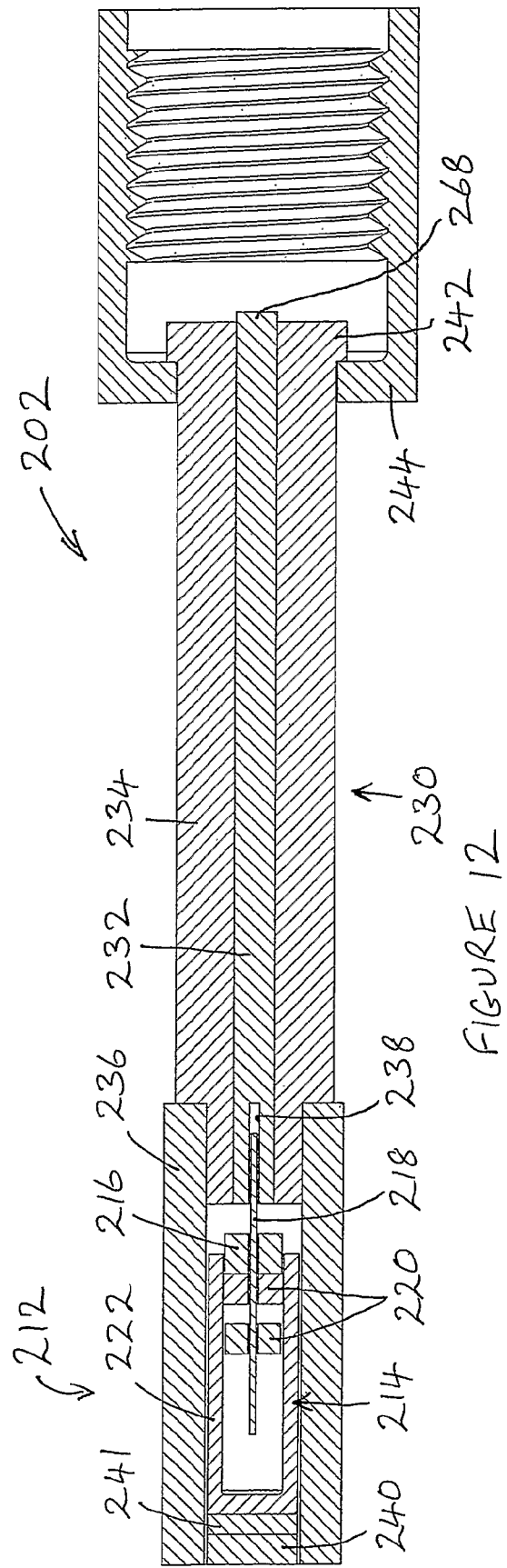
FIG. 12 is a longitudinal section of the probe body of FIG. 11.

The probe body, disassembled from the probe support, is illustrated in FIGS. 11 and 12. It comprises a probe chamber 212 in which a sensor 214 is received. The sensor structure is similar to that illustrated in FIG. 2, comprising a blind-ended tube, or thimble, 222 of solid-electrolyte material provided with platinum electrodes formed on the inner and outer surfaces of the blind end of the tube. The tube is 13 mm long and of 4.5 mm outside diameter. The tube contains a metal/metal-hydride reference material (not shown) and is sealed with a sensor cap 216. An electrode wire 218 extends through a hole in the sensor cap and is connected, within the sensor body, to the reference electrode on the inner surface of the sensor cavity (not shown). Inert spacers 220 retain the metal/metal-hydride reference material in position within the sensor chamber and reduce the internal volume of the sensor chamber.

The probe-body chamber 212 is at one end of a probe-body shaft 230. The shaft is 44 mm long and 8 mm in diameter and comprises an electrically-conductive core, or rod, of SiC (2 mm diameter) extending axially within an electrically-insulating tube 234 of SiAlON. The SiC rod may, for example, be secured within the SiAlON tube by brazing or by means of a glass seal, or in any other convenient manner.

At one end of the shaft 230, the probe-body chamber 212 is formed by push-fitting a cylindrical tube of AlN (aluminium nitride, 23 mm long, 9 mm outside diameter) 236 on to a reduced-diameter portion at the end of the shaft. The sensor is received within the AlN tube and the electrode wire 218 extends into an axial blind bore 238 formed at the end of the SiC rod 232. Electrical contact is thus automatically made between the electrode wire and the SiC rod as the electrode is received in the probe-body chamber. After the sensor has been inserted into the chamber, followed by a graphite wool spacer 241, a hydrogen-permeable seal or barrier 240 is inserted, as an interference fit to close the chamber and mechanically retain the sensor within it.

The end of the shaft distant from the probe chamber is formed with a radially-extending flange 242 which retains an internally-threaded graphite collar 244. The collar is slidable along the shaft but is held captive between the flange 242 and the AlN sleeve 236, which is of larger external diameter than the SiAlON sleeve 234; during assembly, the graphite collar must be placed on the shaft before the AlN cylinder is push-fitted on to the shaft. FIG. 11 is a side view of the probe body, showing the graphite collar in a position near the middle of the shaft.

Figure 13:
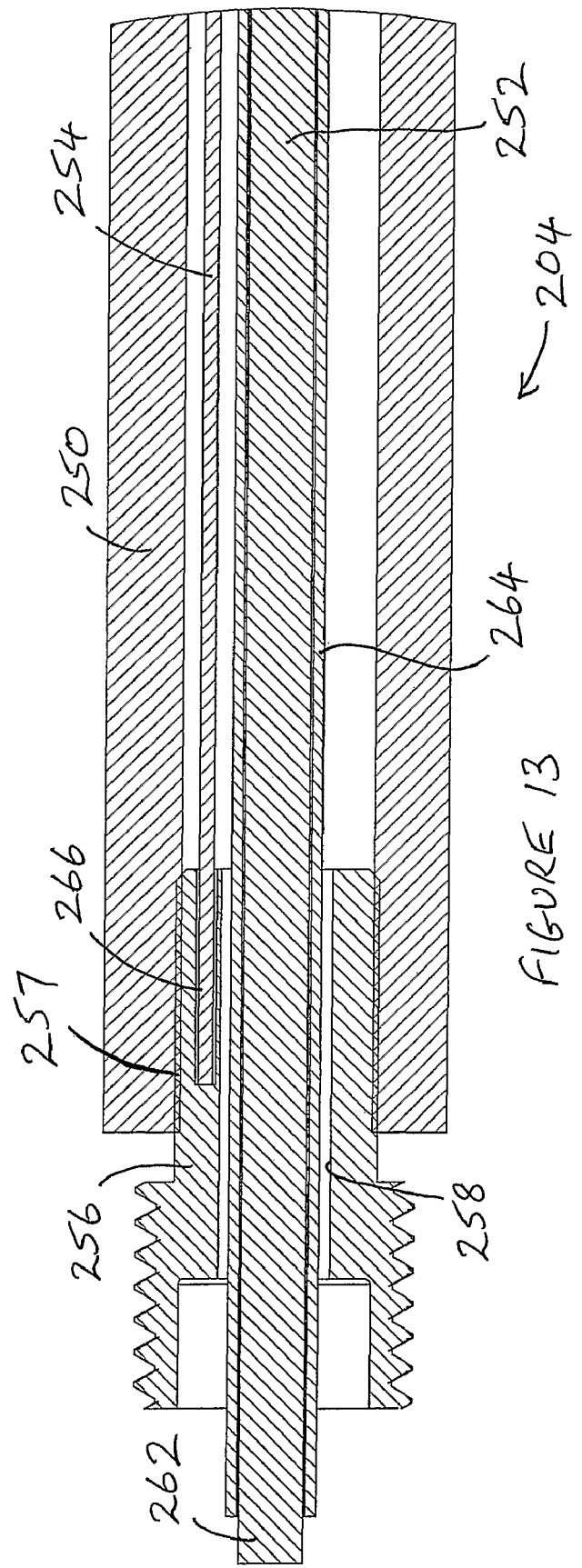
FIG. 13 is a longitudinal section of an end portion of the probe support of the probe of FIG. 10.

FIG. 13 is a longitudinal section of the end of the probe support before it is coupled with the probe body. The support 204 comprises a SiAlON tube 250 approximately 50 cm long and 16 mm outside diameter, within which two electrical conductors extend from the hub 206 for connecting the electronic analyser to the reference electrode and the measurement electrode respectively. These are the reference-electrode conductor 252 and the measurement electrode conductor 254.

At the end of the SiAlON tube to which the probe body is to be coupled, a SiC boss 256 is joined to the tube 250. The external surface of the boss comprises a cylindrical portion which is coated with silver ink, inserted within the end of the tube, and heated to 950C. (the melting point of silver) to secure the joint 257. Other brazing or glassing jointing techniques may also be used. Advantageously, no change in cross section of the SiAlON tube is required, reducing thermal expansion stresses upon immersion of the end of the tube into molten metal. A portion of the boss extending from the end of the tube is externally threaded, for receiving the internal thread of the graphite collar 244.

The reference-electrode conductor 252 is provided by the sheath of an Inconel 600 sheathed thermocouple which extends through the length of the SiAlON tube 250. The sheath of the thermocouple is insulated from the thermocouple wires within it and so can be used as the reference-electrode conductor. The thermocouple sheath 252 is coated with an electrically insulating layer, 264, which insulates the conductor from the boss and within the SiAlON tube. The end of the sheath, and reference-electrode conductor, extends through an axial passage 258 in the boss 256. The sheath is acted upon by a spring 260 at the hub, which urges the opposite end 262 of the sheath away from the end of the SiAlON tube and out of the boss 256.

The measurement-electrode conductor 254 is an Inconel 600 electrode which extends from the hub 206 to an offset blind bore 266 in the boss. The reference-electrode conductor within the SiAlON tube is threaded through ceramic beads (not shown) to ensure electrical insulation from the reference-electrode conductor and from the probe-support tube 250.

Figure 14:
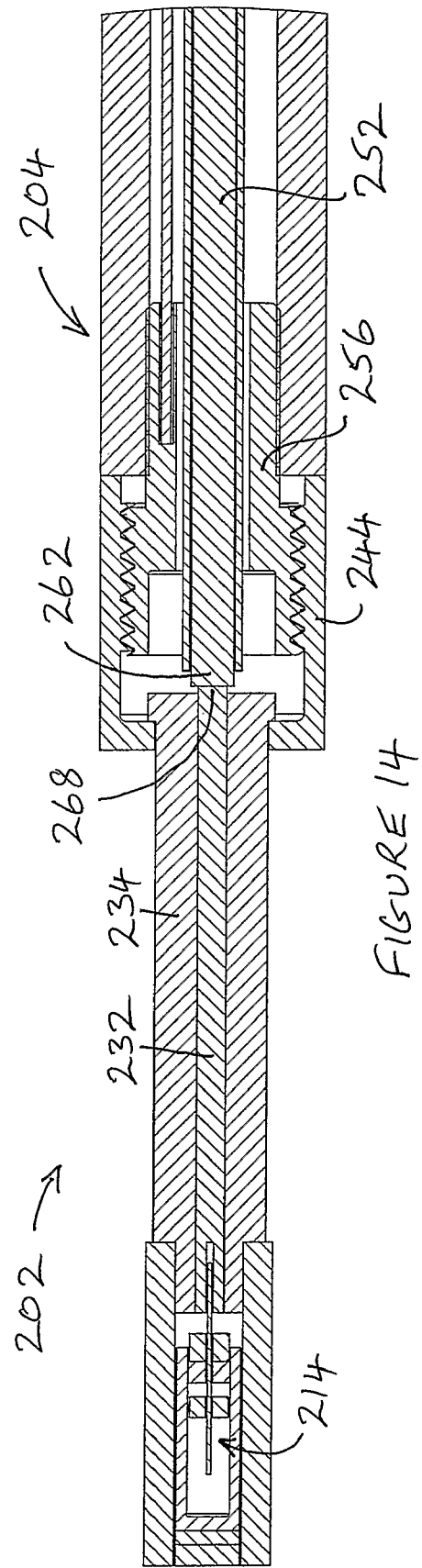
FIG. 14 is a longitudinal section of the probe body and an end of the probe support of the probe of FIG. 10, in assembled form.

To couple the probe body to the probe support, the graphite collar 244 is simply threaded on to the boss 256, as shown in FIG. 14. As the collar is threaded on to the boss, an end 268 of the SiC rod 232 within the probe-body shaft, which stands slightly proud of the end of the SiAlON sleeve 234 of the shaft within the graphite collar, comes into contact with the end 262 of the reference-electrode conductor. As the collar is threaded further on to the boss, this contact urges the reference-electrode conductor into the hub, against the action of the biasing spring 260. This ensures both that good electrical contact is made between the SiC rod and the reference-electrode conductor, and that the flange 242 of the probe-body shaft is firmly seated within the graphite collar. When the collar is fully threaded on to the boss, an end of the collar butts against an end surface of the SiAlON tube 250 of the probe support. The assembled structure can be seen in FIGS. 14 and 15.

In the assembled probe, the reference electrode is electrically connected to the connector 210 at the hub by means of the electrode wire 218, the SiC rod 232 and the reference-electrode conductor 252. The measurement electrode is connected to the connector 210 through the graphite felt 241, the graphite end cap 240, the metal melt, the graphite collar (which in use is submerged in the melt), the SiC boss 256 and the measurement-electrode conductor 254.

Further features of this embodiment of the invention are as follows.

At the hot end of the probe, which is submerged in the melt during use, SiC is used to make reliable high-temperature electrical connections, as required of the rod 232 within the probe-body shaft and at the boss 256. SiC is not subject to oxidation or deterioration under the measurement conditions, on immersion in molten aluminium at temperatures of between 600C and 850C, either under the reducing atmosphere produced by hydrogen evolved from the aluminium or the oxidising atmosphere likely to exist within the probe support tube 250, which is exposed to air at its handle end.

The graphite collar, the flanged end of the probe-body shaft, and the end of the probe support tube 250 can be fabricated to suitable tolerances such that a gasket is not required in order to prevent aluminium ingress at the joint between the probe body and the probe support. This advantageously reduces the complexity of the structure of the joint.

It is desirable to avoid changes in cross section of components that are to be immersed in molten metal. Nevertheless, in the embodiment there is a reduction in cross section of the probe-body shaft to allow fitting of the AlN cylinder, to form the probe-body chamber. However, the push-fit of the AlN cylinder 236 on to the end of the shaft allows a slight relaxation of the joint on immersion in molten aluminium, reducing or preventing stresses. In addition, the materials are selected to be closely matched in thermal expansion, again reducing thermal stresses.

The probe-body shaft separates the sensor cavity from the end of the probe support. The graphite collar seals the end of the probe support against ingress of molten aluminium but it is not gas tight and the inside of the collar is effectively exposed to the atmosphere, as noted above. Thus, an artificially low hydrogen level exists at the end of the probe support. Consequently, the length of the probe-body shaft and the wetting of the shaft by the molten aluminium must be predetermined to prevent any local low hydrogen level affecting the hydrogen activity measured by the sensor.

The hydrogen-permeable seal 240 is preferable made of porous graphite and its porosity can be adjusted to improve the stability of the probe signal while the melt is being treated by gas injection. If a gas bubble is situated directly underneath the graphite membrane, it can cause an undesirable rapid change in the signal from the probe. The probe can be made less sensitive to such rapid local fluctuations in the partial pressure of hydrogen at its end by making the graphite seal less porous. This must be balanced against the requirement for sufficient porosity so that hydrogen diffusion through the seal provides a sufficiently rapid probe-measurement response time.

The external surface of the SiAlON tube 250 of the probe support may be coated with SiC. This will earth the melt, making the probe more resilient to noise, for example in induction-heated furnaces, and will also provide electrical screening of the conductors within the tube. The inside surface of the SiAlON tube may also be coated with SiC and the coating used as the measurement-electrode conductor. The conductor 254 may then be omitted.

As shown in FIG. 10, the probe support is fabricated in two tubular sections 270, 272, coupled at a joint 274. The probe-support section 270 to which the probe body is coupled comprises the SiAlON tube 250 described above. The SiAlON tube 250 and the remaining portion of the probe support 272 are each about 50 cm in length. Since an end portion of the SiAlON tube is immersed in molten metal when hydrogen concentration readings are taken, it may degrade over time, although degradation is slower than for the probe body. Thus, it is advantageous to be able to replace the SiAlON tube 250 as and when excessive degradation occurs. This can conveniently be achieved by releasing the coupling 274, withdrawing the SiAlON tube and the boss 256, and replacing these components. The reference-electrode conductor, the measurement-electrode conductor and the thermocouple need not be replaced, as these can be threaded through the replacement SiAlON tube and boss.

Figure 16:
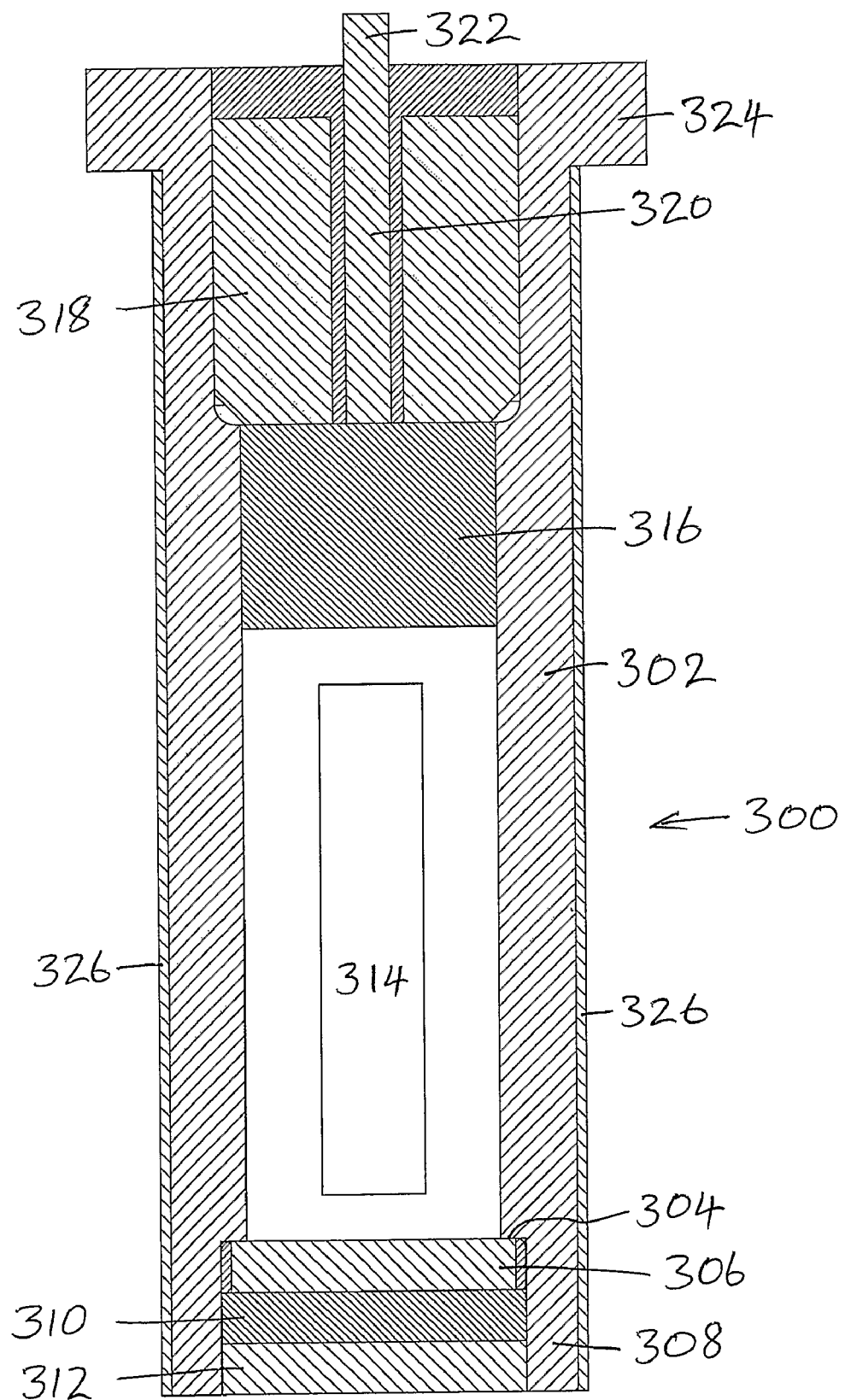
FIG. 16 is a longitudinal section of a probe body incorporating a sensor, according to a further embodiment of the invention.
Figure 17:
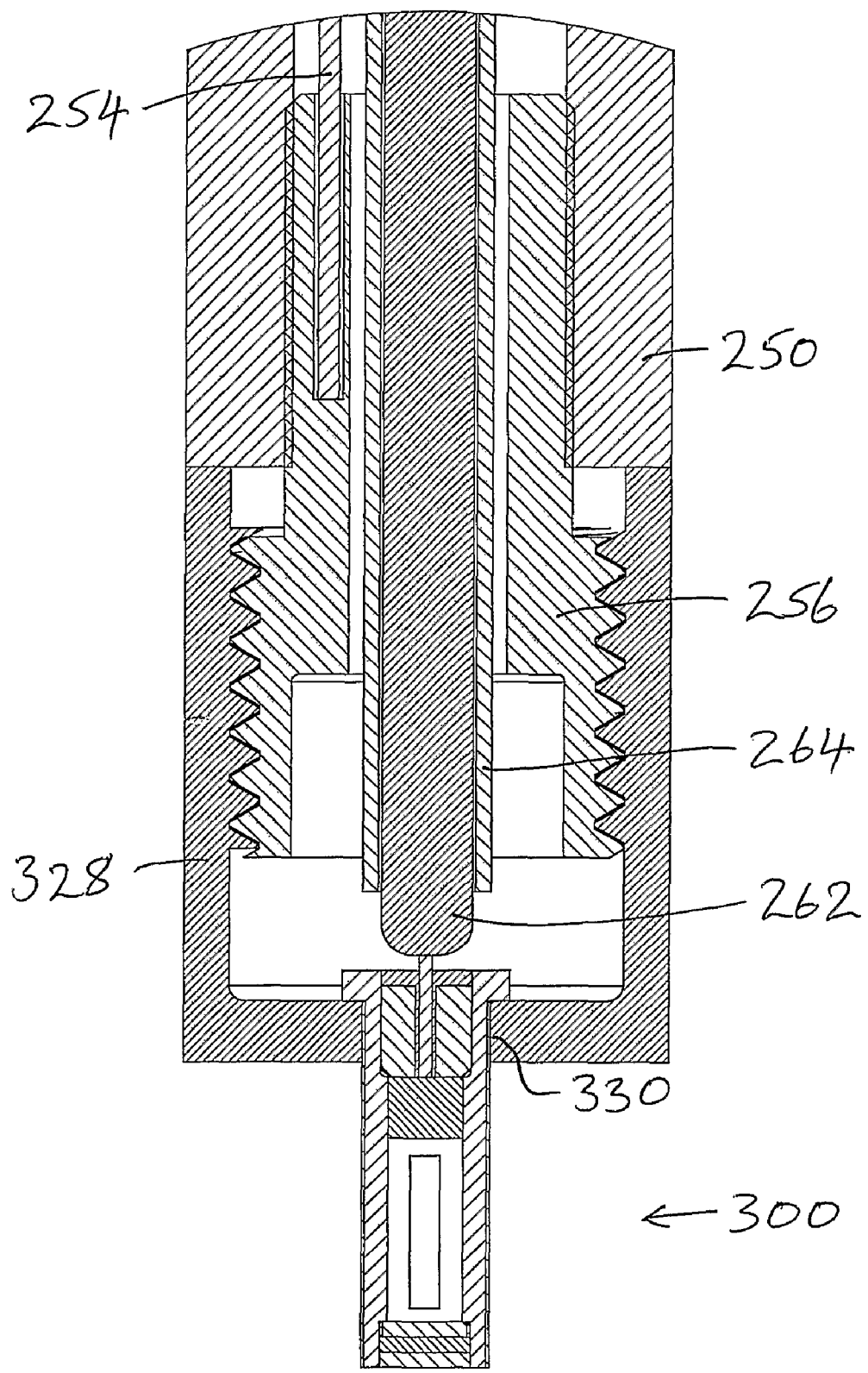
FIG. 17 is a longitudinal section of the probe body and sensor of FIG. 16, coupled to a probe support.

FIGS. 16 and 17 illustrate a further embodiment of the invention in which the functions of the probe body and the sensor are integrated into a single unit. The sensor 300 comprises a sensor tube 302 that is formed with a recessed internal step 304 on which a planar disc of solid electrolyte 306 is seated, and bonded in place. The step is recessed such that an end portion 308 of the sensor tube extends beyond the solid-electrolyte disc. A disc of graphite wool 310 is inserted into this recess, followed by a hydrogen-permeable, push-fitting, graphite disc 312. Within the sensor tube, behind the solid-electrolyte disc, the sensor structure is similar to that described in various embodiments above, including that of FIG. 1.

The tube contains a solid-state hydrogen-reference material 314, packing material 316 and a sensor cap 318.

A measurement electrode is formed on an outer surface of the solid-electrolyte disc and a reference electrode on its inner surface. The measurement electrode contacts the graphite wool and thus, through the hydrogen-permeable graphite seal, is in electrical contact with the melt. The reference electrode is connected to an electrical conductor within the sensor tube (not shown) and thus to a reference-electrode conductor 320 which extends axially through a hole in the sensor cap to terminate standing proud of the upper end of the sensor 322.

The sensor tube 302 is formed at its end adjacent the sensor cap with a flange 324 that extends radially outwards from the tube.

The external surface of the sensor tube is coated with a protective thermal-shock-resistant coating 326.

Figure 15:
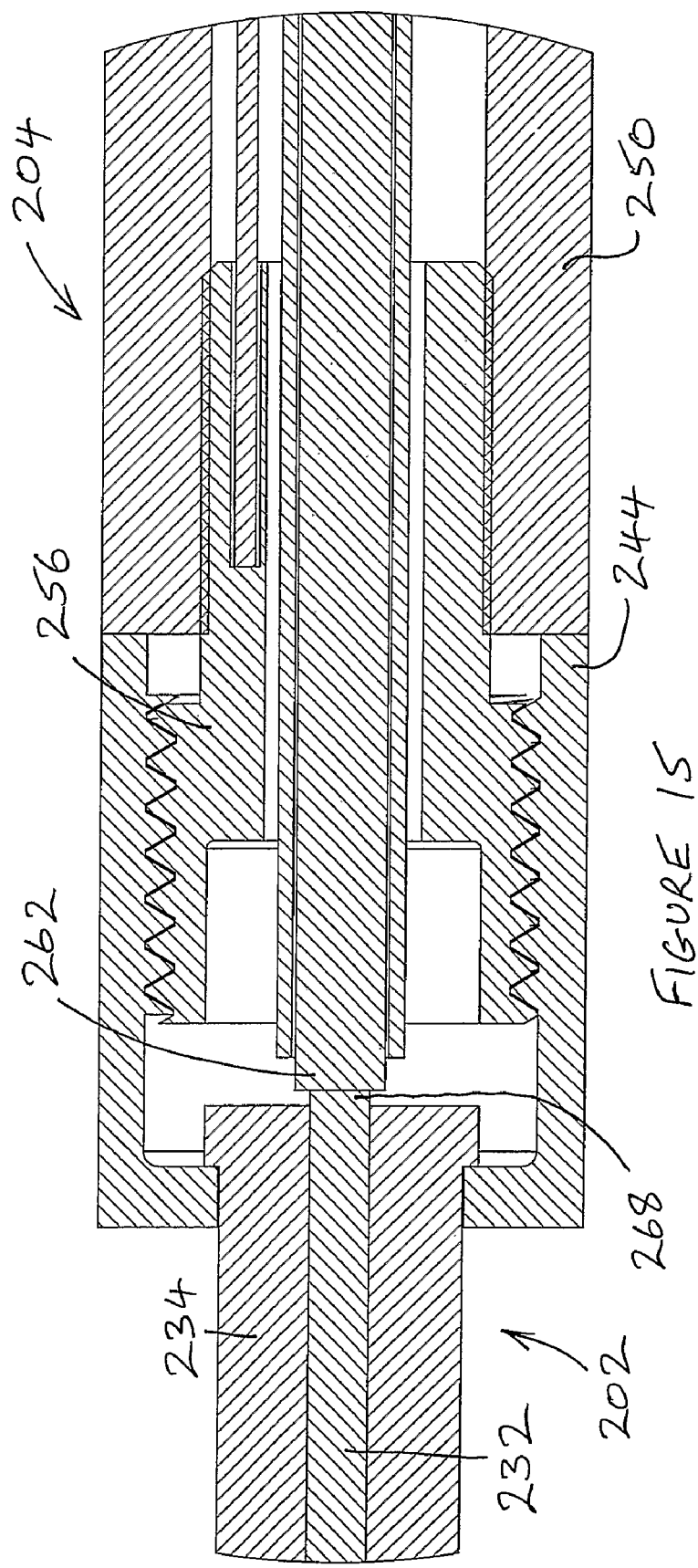
FIG. 15 is an enlarged view of the coupling between the probe body and the probe support of FIG. 14.

FIG. 17 illustrates the coupling of the probe body and sensor 300 to a probe support, which is the same as illustrated in FIGS. 13, 14 and 15. A graphite collar 328 is internally threaded for engagement on the threaded hub 256 and the end of the probe support, and is formed with an axial hole 330 for receiving the probe body and sensor, such that the flange 324 engages an inner surface of the collar. Thus, as the collar is threaded onto the hub, the reference-electrode conductor 322 makes contact with the spring-loaded thermocouple sheath 262, which serves as the reference-electrode conductor within the probe support, as described in relation to FIGS. 13 to 15.

The measurement-electrode is electrically connected through the graphite wool, the graphite seal, the melt and the graphite collar, in the same way as in previous embodiments.

It can be seen that in this embodiment the probe body may be integral with the sensor and comprise a coupling means (in this embodiment the graphite collar) to provide a probe-body unit which is releasably couplable to the probe support.

Electronic Analyser

As described above, the current-reversal measuring technique may be used to measure hydrogen concentration using the probe, and to monitor dehydration of the sensor electrolyte. It is also possible, however, to use a conventional impedance analysis unit. In this case, the analyser measures sensor EMF, temperature, and sensor impedance. Only EMF and temperature are required to calculate dissolved hydrogen level; impedance is used in a different set of calculations to determine sensor condition, as described below.

An EMF is generated between the sensor electrodes according to the Nernst Equation for a hydrogen ion conductor (1):

$$EMF = \frac{RT}{2F} \ln \frac{\mathrm{pH}_2^{ref}}{\mathrm{pH}_2^{meas}} \quad (1)$$

The reference hydrogen partial pressure inside the sensor (pH2ref) is temperature dependent. The analyser is programmed with two calibration values (A and B) which allow it to work out what the reference hydrogen partial pressure is at any given temperature. These calibration values are obtained by measuring the sensor EMF in a known partial pressure of hydrogen at two different temperatures.

The partial pressure of hydrogen in equilibrium with molten aluminium is related to the concentration of dissolved hydrogen (H) by Sievert's law (2):

$$\log H = \frac{1}{2} \log \mathrm{pH}_2^{meas} - \frac{C}{T} + D \quad (2)$$

The constants C and D depend upon the aluminium alloy and vary according to how much the chemistry of the different alloys (e.g. silicon content, magnesium content etc) affects hydrogen solubility.

So, effectively the calculation can be broken down into the following stages:
(i) From the measured temperature, work out the reference hydrogen pressure inside the sensor;
(ii) From the measured EMF and (i), use equation (1) to work out the partial pressure of hydrogen in equilibrium with molten aluminium;
(iii) Use (ii) and equation (2) to work out the concentration of dissolved hydrogen in the melt.

In reality, this can all be combined into one equation (temperature T in degrees Centigrade here).

$$H = 10^{\left\{\frac{5.03913}{T+273}\left(A + \frac{(T-700)}{50}(B-A) - EMF\right) - \frac{C}{T+273} + D\right\}}$$

The analyser also monitors sensor impedance, or resistance, to determine sensor condition as follows. Two calibration constants, $R_{700}$ and $R_{750}$, which are the resistance of the sensor after manufacture at 700C and 750C respectively, are measured and programmed into the analyser. The resistance of the sensor in its as-manufactured, hydrated state can then be calculated at any temperature using the Arrhenius dependence of conductivity on temperature. The analyser monitors the sensor's actual resistance and measures its deviation from the calculated value, and flags any deviation greater than a predetermined threshold, such as 5 kOhms deviation. This strategy provides an accurate indication of the condition of the electrolyte, and allows the analyser to display an appropriate error message if the sensor becomes dehydrated. The temperatures 700C and 750C are arbitrary; other calibration temperatures could be used.

Other Metals

The embodiments described above have been presented in the context of a probe for measuring hydrogen concentration dissolved in molten aluminium and aluminium alloys. A similar probe may be used to measure hydrogen concentration dissolved in molten magnesium and its alloys; any modifications required to ensure materials compatibility with molten magnesium could be carried out by the skilled person without inventive effort. With modification to the embodiments, similar probes could be applied to measure hydrogen concentration dissolved in molten copper and its alloys. The maximum operating temperature of the sensors described in the embodiments is approximately 850° C., beyond which temperature the performance of the metal-metal hydride reference degrades. Molten copper is typically at a temperature of about 1100° C. In order to measure hydrogen concentration in molten copper, the probe body would therefore need to be extended in order to locate the sensor further away from the melt so as to keep the sensor temperature below 850° C.

In conclusion, it can seen that the invention in its various embodiments overcomes many of the disadvantages of prior art hydrogen sensors. These advantages include the following.

Portability

The described embodiments provide a portable probe which can easily be transported to different measuring locations in a foundry. Only the light-weight, solid-state probe and the associated analyser needs to be transported. In addition, the good portability and fast response time of the probe may advantageously allow batch measurements to be made, for example so that a quick check of dissolved hydrogen level can be performed prior to casting.

Suitability for Repeated Immersion

The sensor in the embodiments is self-contained and may advantageously not be joined or sealed to the probe body. Thus, the sensor may advantageously not be subject to physical constraint by the probe body, and the associated forces resulting from thermal expansion mismatch, as in prior art designs. This may advantageously improve the sensor's resistance to thermal cycling and is make the probe suitable for repeated immersion in molten metal.

As a probe is repeatedly dipped in and out of the melt, particularly for molten aluminium, a blocking oxide layer (e.g. of aluminium oxide) can build up which impedes the exchange of hydrogen between the melt and the probe chamber. This can slow down response time and can cause the chemical potential of hydrogen at the sensor's measurement electrode to fall below the equilibrium level in the melt, upon repeated immersions. In prior art probes, this blocking oxide layer builds up due to the reaction between oxygen in air contained in the probe chamber and the molten metal. The self-contained nature of the sensor and probe of the embodiments described herein allows the probe chamber to be designed with a minimum of dead volume (free chamber volume), which may advantageously alleviate both the problems of slow response time and reducing hydrogen-concentration measurement observed in prior art probes after repeated immersions.

Low Cost per Measurement

Prior art measuring techniques suffer from high cost per measurement due to the high cost and short lifetime of hydrogen probes. The embodiments of the present invention described herein enable the use of replacement components, including replacement sensors, which may advantageously be manufactured more cheaply and enable the probe to remain in service for longer. Consequently, the cost per measurement may advantageously be reduced by comparison with prior art techniques.

On-Line Monitoring of the Degassing Process

The embodiments of the present invention are of advantageously robust construction and may enable rapid response to changes in dissolved hydrogen level. These probes may therefore be used in conjunction with a rotary degasser for on-line, real-time monitoring of the degassing process.

Conclusion

Important advantages of the embodiments of the invention include the self-contained nature of the sensor and the portability of the probe. The self-contained nature of the sensor is exploited in various ways. First, the sensor is preferably not joined or bonded to the probe body, which may dramatically improve the thermal shock resistance of the sensor and lead to longer sensor lifetime in terms of cycles to failure. Second, the probe body and the sensor may preferably be miniaturised, giving the following benefits; reducing the dead volume in the probe chamber may advantageously improve response time to changes in hydrogen concentration and prevent accumulation of metal oxide on the probe surface upon repeated immersion; the pre-heat time of the probe on immersion may be advantageously reduced and the probe's thermal shock resistance improved. Finally, the cost of manufacture of the probe and replacement sensors may be advantageously low.

The invention claimed is:

1. A probe having a probe body comprising a hydrogen sensor, the sensor comprising;
    a sensor body having a wall within which a sealed cavity is defined, the cavity containing a solid reference material for generating a reference partial pressure of hydrogen within the cavity;
    a solid electrolyte forming at least a portion of the wall;
    a measurement electrode on a surface of the solid electrolyte outside the cavity;
    a reference electrode on a surface of the solid electrolyte within the cavity, exposed to the reference partial pressure of hydrogen; and
    an electrical conductor extending from the reference electrode through the wall to an external surface of the sensor body;
    and in which the body comprises:
    a chamber for receiving the sensor; and
    a reference-signal connection for connecting to the electrical conductor when the sensor is received in the chamber.

2. The probe according to claim 1, in which the probe body is integral with the sensor, optionally comprising a coating on the external surface of the sensor.

3. The probe according to claim 2, in which the probe body comprises a coupling means for removably coupling the probe body and the sensor to a probe support.

4. The probe according to claim 1, in which the sensor body comprises a tube, the solid electrolyte closing one end of the tube and a sensor cap closing the other end of the tube, the sensor cap preferably comprising the same material as the tube.

5. The probe according to claim 4, in which the electrical conductor extends through the sensor cap.

6. The probe according to claim 1, in which the sensor body comprises the solid electrolyte in the form of a tube, closed at one end, and a sensor cap closing the other end of the tube.

7. The probe according to claim 1, in which the electrical conductor extends outwardly from an outer surface of the sensor body, and the reference-signal connection comprises a socket for contacting the electrical connector when the sensor is received in the chamber.

8. The probe according to claim 1, in which the probe chamber comprises a measurement-signal connection or connector for electrically connecting to the measurement electrode when the sensor is received in the chamber.

9. The probe according to claim 1, in which the chamber comprises an opening which is sealable by means of a hydrogen-permeable seal, the seal optionally retaining the sensor within the chamber.

10. The probe according to claim 9, in which the hydrogen-permeable seal comprises a non-conductive material such as porous alumina, porous silicon carbide or porous silicon nitride, and is optionally coated with a wetting agent such as titanium diboride.

11. The probe according to claim 9, in which the hydrogen-permeable seal is electrically conductive and comprises graphite or a porous metal and optionally makes electrical connection with the measurement electrode, is optionally coated with a wetting agent such as titanium diboride, and is optionally connected to an earthing conductor.

12. The probe according to claim 9, further comprising an insert positioned between the hydrogen-permeable seal and the sensor.

13. The probe according to claim 9, in which the hydrogen-permeable seal is held in place by a screw thread or by an interference fit.

14. The probe according to claim 9, in which the chamber is sealed except at the opening.

15. The probe according to claim 9, in which the sensor is insertable through the opening into the chamber.

16. The probe according to claim 1, in which the sensor is removable from the chamber, and optionally is replaceable.

17. The probe according to claim 1, in which when the sensor is inserted into the chamber, there is sufficient clearance between the sensor body and the chamber to accommodate thermal shocks in use without application of excessive stresses to the sensor.

18. The probe according to claim 1, in which when the sensor is inserted into the chamber, there is sufficient clearance between the sensor body and the chamber to allow hydrogen flow between the sensor and the chamber.

19. The probe according to claim 1, in which the sensor body is a loose fit in the chamber.

20. A probe having a probe body comprising a hydrogen sensor, the sensor comprising:
- a sensor body having a wall within which a sealed cavity is defined, the cavity containing a solid reference material for generating a reference partial pressure of hydrogen within the cavity;
- a solid electrolyte forming at least a portion of the wall;
- a measurement electrode on a surface of the solid electrolyte outside the cavity;
- a reference electrode on a surface of the solid electrolyte within the cavity, exposed to the reference partial pressure of hydrogen; and
- an electrical conductor extending from the reference electrode through the wall to an external surface of the sensor body;
- and in which the probe body is integral with the sensor, and in which the probe body comprises a coupling means for removably coupling the probe body and the sensor to a probe support.

21. A probe having a probe body comprising a hydrogen sensor, the sensor comprising:
- a sensor body having a wall within which a sealed cavity is defined, the cavity containing a solid reference material for generating a reference partial pressure of hydrogen within the cavity;
- a solid electrolyte forming at least a portion of the wall;
- a measurement electrode on a surface of the solid electrolyte outside the cavity;
- a reference electrode on a surface of the solid electrolyte within the cavity, exposed to the reference partial pressure of hydrogen; and
- an electrical conductor extending from the reference electrode through the wall to an external surface of the sensor body;
- and in which the sensor body comprises a tube, the solid electrolyte closing one end of the tube and a sensor cap closing the other end of the tube, the sensor cap comprising the same material as the tube.

22. The probe according to claim 21, in which the electrical conductor extends through the sensor cap.

* * * * *